United States Patent [19]
Khorasani et al.

[11] Patent Number: 6,029,138
[45] Date of Patent: Feb. 22, 2000

[54] COMPUTER SYSTEM FOR DECISION SUPPORT IN THE SELECTION OF DIAGNOSTIC AND THERAPEUTIC TESTS AND INTERVENTIONS FOR PATIENTS

[75] Inventors: Ramin Khorasani, Newton; David W. Bates, Watertown; Michael Viera, West Roxbury; Brian Chiango, Medford, all of Mass.

[73] Assignee: Brigham and Women's Hospital, Boston, Mass.

[21] Appl. No.: 08/911,790

[22] Filed: Aug. 15, 1997

[51] Int. Cl.[7] .................................................. G06F 17/60
[52] U.S. Cl. ..................... 705/2; 705/1; 705/3; 600/300; 600/301
[58] Field of Search ....................... 705/2, 3, 1; 600/300, 600/301; 128/923

[56] References Cited

U.S. PATENT DOCUMENTS

| | | | |
|---|---|---|---|
| 4,315,309 | 2/1982 | Coli .............................................. | 705/3 |
| 4,731,725 | 3/1988 | Suto et al. ............................... | 128/923 |
| 4,852,570 | 8/1989 | Levine ..................................... | 600/301 |
| 5,025,374 | 6/1991 | Roizen et al. ........................... | 600/300 |
| 5,262,943 | 11/1993 | Thibado et al. ......................... | 600/300 |
| 5,265,010 | 11/1993 | Evans-Paganelli et al. ............. | 600/301 |
| 5,341,291 | 8/1994 | Roizen et al. ................................ | 705/2 |
| 5,517,405 | 5/1996 | McAndrew et al. .......................... | 705/2 |
| 5,519,607 | 5/1996 | Tawil ........................................... | 705/2 |
| 5,583,758 | 12/1996 | McIlroy et al. .............................. | 705/2 |
| 5,619,991 | 4/1997 | Sloane .................................... | 600/300 |
| 5,675,786 | 10/1997 | McKee et al. .............................. | 705/33 |
| 5,819,229 | 10/1998 | Boppe ......................................... | 705/2 |
| 5,890,129 | 3/1999 | Spurgeon .................................... | 705/2 |

OTHER PUBLICATIONS

B. Roessink et al., Computers in Cardiology Problem–Oriented Access to Clinical Literature on Acute Cardiac Ischemia, The Institute of Electrical and Electronics Engineering, Inc., pp. 729–732, Sep. 1991.

B. Roessink, et al., Computers in Cardiology, Problem–Oriented Access to Clinical Literature on Acute Cardiac Ischemia, Sep. 23–26, 1991, The Institute of Electrical and Electronics Engineers, Inc., pp. 729–732.

*Primary Examiner*—Emanuel Todd Voeltz
*Assistant Examiner*—John Hayes
*Attorney, Agent, or Firm*—Wolf, Greenfield & Sacks, P.C.

[57] ABSTRACT

A decision support system for the selection of a diagnostic or therapeutic test or intervention, herein called studies, is supported by identifying a relative number of cases in which significant results were obtained in studies having the same indications. In particular, an ordering physician requests a study for a patient and specifies indications for the study, such as symptoms and a potential diagnosis. The number of studies performed, including those on other patients, for which results were significant for the same indications out of the total number of studies performed for the same indications is provided as feedback to the ordering physician. This feedback relates actual patient results to the appropriateness of the study. A decision support system in a health care information management system receives, from an ordering physician, an order for a study to be performed on a specified patient and indications for the study. The received indications for the selected study are used to access a database of result codes for previous studies having the same indications, including studies performed on other patients. A result of the comparison of the selected study and specified indications to the result codes database is then sent to the ordering physician. Decision support may be enhanced by using data extracted from existing scientific literature. In one embodiment, the decision support system is part of a health care management system that supports structured order entry for use by the ordering physician and a structured data entry module for entering result codes into the database.

11 Claims, 6 Drawing Sheets

60 — 1. Are history and/or symptoms and/or signs presented on the requisition?
   Y: yes
   N: no 62 — 2. Did you get additional clinical information?
   Y: yes
   N: no 64 — 3. In your opinion, the study is:
   Y: indicated
   N: not indicated 66 — 4. Results:
   P: Positive and clearly related to the clinical information
   N1. Normal.
   N2. Abnormal, likely significant
   N3. Abnormal, likely insignificant.
   N4. Abnormal, significance not determined.

P.S. Significance of an abnormality is defined as to when the referring physician will likely take an action based on this result, in your opinion. You can only use one of the codes for the results (P,N1,N2,N3,N4,Q)

Q: Equivocal.

68 — 5. Is there any change from prior study? (by report or direct comparison)
   U: unchanged
   C: change
   O: no priors

FIG. 3

| GI/GU Fluoroscopy -- IVP/IVU |||
|---|---|---|
| Relevant History (choose at least one) |||
| ☒ Acute flank pain | ☐ Post-op (specify below) | |
| ☐ Recurrent flank pain | ☐ Benign prostatic hyperplasia | |
| ☒ Hematuria | ☐ Reflux nephropathy | |
| ☐ Urolithiasis/nephrolithiasis | ☐ Incontinence | |
| ☐ Recurrent UTI | ☐ Renal insufficiency | |
| ☐ Trauma | ☐ Hypertension | |
| Other: |||
| R/O or Assess (choose at least one) |||
| ☒ Obstructive uropathy | ☐ Post-op complications | |
| ☐ Renal mass | ☐ Anatomy | |
| ☐ Nephro/urolithiasis | ☐ Pyleonephritis | |
| ☐ Urothelial lesion | ☐ Renal artery stenosis | |
| ☐ Vesicoureterio reflux | | |
| Other: |||

74 points to the Relevant History checkboxes; 70 brackets the Relevant History section; 76 points to Obstructive uropathy; 72 brackets the R/O or Assess section.

Additional clinical history (optional):

[ Enter ]  [ Reset ]

Exam ordered: GI/GU/Fluoro.Intravenous urogram ~80
History:

- Acute flank pain } 82
- Hematuria

Ruleout/Assess:

- Obstructive uropathy } 84

86
[ Cancel ]  Cancel this order and re-order

88 { Dedicated ureter CT performed without oral or intravenous contrast and equal in charges to an intravenous urogram, is the examination of choice in the initial evaluation of acute renal colic.

( File Request (site and time to be determined) )

90 {
Select a facility to perform the exam: [ BWH - Main Campus ]

Select a time to perform the exam: [ Tomorrow ]   Date (mm/dd/yy): [    ]

Indicate patient pregnancy status: [ Not pregnant ]

( Complete Request )

FIG. 7

A
COMPUTER SYSTEM FOR DECISION SUPPORT IN THE SELECTION OF DIAGNOSTIC AND THERAPEUTIC TESTS AND INTERVENTIONS FOR PATIENTS

FIELD OF THE INVENTION

The present invention is related to information systems for use in a health care setting, particularly for providing decision support in the selection of diagnostic and therapeutic tests and interventions for patients.

BACKGROUND OF THE INVENTION

Diagnostic and therapeutic tests and interventions, including imaging studies, radiology tests, prescriptions and various other procedures, are a significant portion of health care expenditures. In an effort to improve the quality and cost effectiveness of medical care, increasing emphasis has been placed on reducing inappropriate utilization of tests and interventions. It is believed that the reduction of inappropriate tests and interventions also may improve the quality of care by sparing patients from unnecessary procedures which may delay time to reach a correct diagnosis or may subject the patient to unnecessary risks.

Several methods have been implemented to manage utilization of tests and interventions. These methods include education in the form of expert opinion, precertification for expensive tests, profiling of a physician's ordering behavior for comparison to standards and other colleagues' profiles, capitation of the number of tests or interventions, consultation services, and case-based reasoning systems.

In the "Clearing the Way for Physician's Use of Clinical Information Systems" by James G. Anderson, in *Communications of the ACM,* August 1997, Vol. 40, No. 8, pp. 83–90, it is noted that there are many barriers to direct physician use of clinical information systems. In particular systems that either seek to change the physician's behavior or interfere with traditional practice routines are often not adopted readily by physicians.

When a system is accepted by physicians, there is also the risk that the system may reinforce bad practices by being based on assumptions about appropriateness of various procedures. For example, in systems using case-based reasoning, a physician's experience is used as a knowledge base of cases. A test for a patient is selected according to the test used for patients having similar indications. In "Case-Based Reasoning and Imaging Procedure Selection" by Charles A. Kahn, Jr., in *Investigative Radiology,* Vol. 29, p. 643 (June 1994), it is noted that one potential disadvantage with case-based reasoning is that such a system tends to follow the practices of its teachers, even if those practices are not optimal or up-to-date according to established practiced guidelines.

Even the establishment of practice guidelines may be difficult because there is often disagreement among physicians as to the appropriateness of various procedures. See, for example, "Appropriateness of Imaging Procedure Requests: Do Radiologists Agree" by Charles E. Kahn, Jr., et al., in AJR, Vol. 169, p. 11, July 1997. This reference indicates the lack of knowledge about the relationship between appropriateness of a procedure and actual patient outcomes.

SUMMARY OF THE INVENTION

The present invention provides decision support in the selection of a diagnostic or therapeutic test or intervention, herein called studies, by identifying a relative number of cases in which significant results were obtained in studies having the same indications. For example, assuming an ordering physician requests an x-ray examination, where the indications for the x-ray are a persistent cough and to detect pneumonia. The number of studies performed, including those on other patients, for which results were significant for the same indications out of the total number of studies performed for the same indications is provided as feedback to the ordering physician. This feedback relates actual patient results to the appropriateness of the study.

Accordingly, one aspect of the present invention is a decision support system in a health care information management system. This system receives, from an ordering physician, an order for a study to be performed on a specified patient and indications for the study. The received indications for the selected study are used to access a database of result codes for previous studies having the same indications, including studies performed on other patients. A result of the comparison of the selected study and specified indications to the result codes database is then sent to the ordering physician. In one embodiment, the decision support system is part of a health care management system that supports structured order entry for use by the ordering physician and a structured data entry module for entering result codes into the database.

These and other aspects and advantages of the present invention will be better understood in view of the following detailed description and appended drawings.

DETAILED DESCRIPTION

The present invention will be more completely understood through the following detailed description which should be read in conjunction with the attached drawing in which similar reference numbers indicate similar structures. All references cited herein are hereby expressly incorporated by reference.

In the present invention, decision support is evidence-based, i.e., specified indications for a selected study are compared to actual results for previous studies having the same indications, to determine the likelihood that significant results will be obtained from the study. Where available, data from existing scientific literature also may be used to enhance the online decision support. Such feedback is provided to the ordering physician by either denying the request, approving the request, or suggesting an alternative study.

Figure 1:
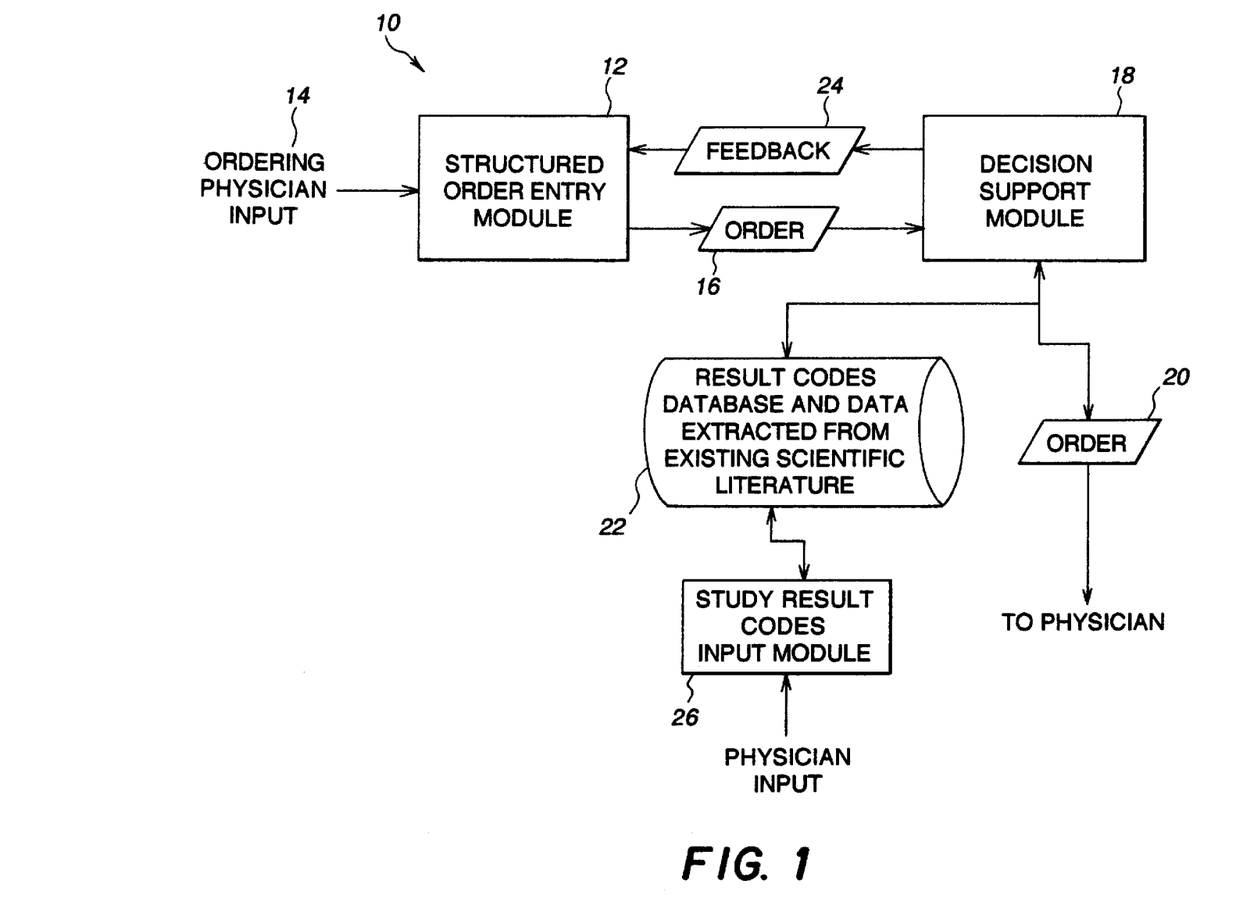
FIG. 1 is a block diagram of the computer system in one embodiment of the present invention.

One embodiment of a health care information management system implementing this form of decision support is shown in FIG. 1. The system 10 includes a structured order entry module 12 through which an ordering physician provides input 14 to generate an electronic order form 16, requesting a test or intervention, herein called studies, for a patient, along with the indications, or reasons, for the study. The structured order entry module 12, described in more detail below, may be implemented, for example, by using a set of integrated menus. One menu may list studies which may be selected. Another menu may list indications for the study which may be specified.

A decision support module 18 receives the order and may send the order to the appropriate radiologist or other physician to schedule and perform the selected study, as indicated at 20. However, the decision support module 18 also compares the selected study and specified indications for the study to a result codes database 22 to provide some measure of the appropriateness of the requested study, i.e., the likelihood that the study will provide significant results. How this comparison is performed by the decision support module is described in more detail below in connection with FIG. 6. The decision support module 18 provides feedback 24 to the ordering physician, for example by means of some graphical user interface. While FIG. 1 shows the feedback as being directed to the structured order entry module, it may be a separate document displayed in an HTML browser to the ordering physician, for example. The result codes database 22, for which records are described in more detail below, is built by input of actual result codes for various patients by study result codes input module 24. The kinds of information that are included in the result codes database are the kind of study, indications for the study, and a code describing the results of the study.

The system as described in FIG. 1 may be implemented using a computer system programmed using appropriate software. Each of the modules 12, 18, 22 and 24 may be implemented on a single machine or on separate machines connected through a computer network, in which case the modules communicate via an appropriate protocol, such as TCP/IP. A suitable computer system to implement the system 10 or computer 12 typically includes an output device which displays information to a user. The computer system includes a main unit connected to the output device and an input device, such as a keyboard. The main unit generally includes a processor connected to a memory system via an interconnection mechanism. The input device is also connected to the processor and memory system via the connection mechanism, as is the output device.

It should be understood that one or more output devices may be connected to the computer system. Example output devices include a cathode ray tube (CRT) display, liquid crystal displays (LCD), printers, communication devices such as a modem, and audio output. It should also be understood that one or more input devices may be connected to the computer system. Example input devices include a keyboard, keypad, track ball, mouse, pen and tablet, communication device, audio input and scanner. It should be understood the invention is not limited to the particular input or output devices used in combination with the computer system or to those described herein.

The computer system may be a general purpose computer system which is programmable using a high level computer programming language, such as "C++." The computer system also may be specially programmed, special purpose hardware. In a general purpose computer system, the processor is typically a commercially available processor, of which the series x86 processors, available from Intel, and the 680X0 series microprocessors available from Motorola are examples. Many other processors are available. Such a microprocessor executes a program called an operating system, of which windows 95 or NT, UNIX, DOS and VMS are examples, which controls the execution of other computer programs and provides scheduling, debugging, input/output control, accounting, compilation, storage assignment, data management and memory management, and communication control and related services. The processor and operating system define a computer platform for which application programs in high-level programming languages are written.

A memory system typically includes a computer readable and writeable nonvolatile recording medium, of which a magnetic disk, a flash memory and tape are examples. The disk may be removable, known as a floppy disk, or permanent, known as a hard drive. A disk has a number of tracks in which signals are stored, typically in binary form, i.e., a form interpreted as a sequence of one and zeros. Such signals may define an application program to be executed by the microprocessor, or information stored on the disk to be processed by the application program. Typically, in operation, the processor causes data to be read from the nonvolatile recording medium into an integrated circuit memory element, which is typically a volatile, random access memory such as a dynamic random access memory (DRAM) or static memory (SRAM). The integrated circuit memory element allows for faster access to the information by the processor than does the disk. The processor generally manipulates the data within the integrated circuit memory and then copies the data to the disk when processing is completed. A variety of mechanisms are known for managing data movement between the disk and the integrated circuit memory element, and the invention is not limited thereto. It should also be understood that the invention is not limited to a particular memory system.

It should be understood the invention is not limited to a particular computer platform, particular processor, or particular high-level programming language. Additionally, the computer system may be a multiprocessor computer system or may include multiple computers connected over a computer network.

Figure 2:
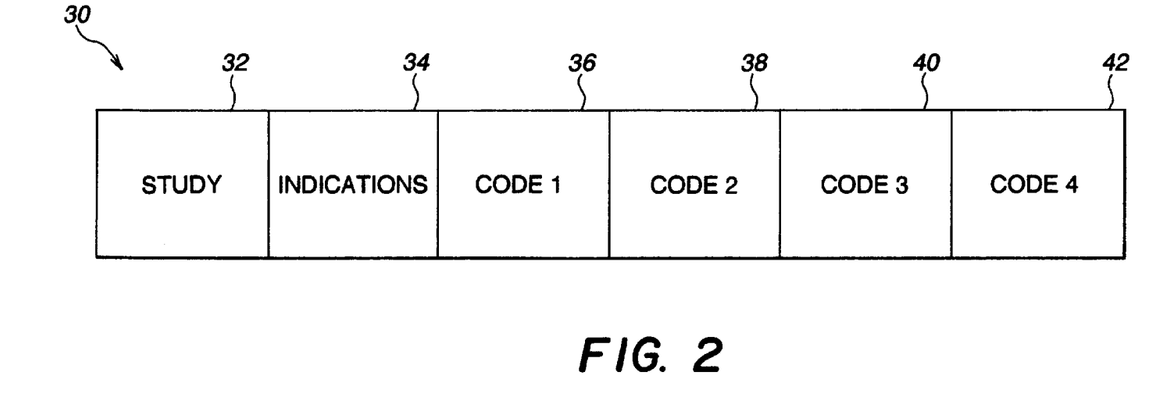
FIG. 2 is an illustration of a data record in a relational database for storing result codes of a study performed on a patient.

An example implementation will now be described in connection with FIGS. 2 through 6. FIG. 2 illustrates a sample record that may be found in the result codes database 22. This record 30 specifies the study 32, the indications for the study 34 and various fields for result codes 36 through 42. One of the result codes, e.g., code 1, indicates whether the results are significant and clearly related to the clinical information or not. This record 30 may be found in a relational database that is used to implement the result codes database 32. This database should be structured such that a query may be run to identify the total number of records for the selected study and specified indications, and a number of those total records in which the result code shows that the study findings were significant and related to the clinical information. The database also may include decision support information that is extracted from existing scientific literature and associated with a study and a set of indications for the study.

Figure 3:
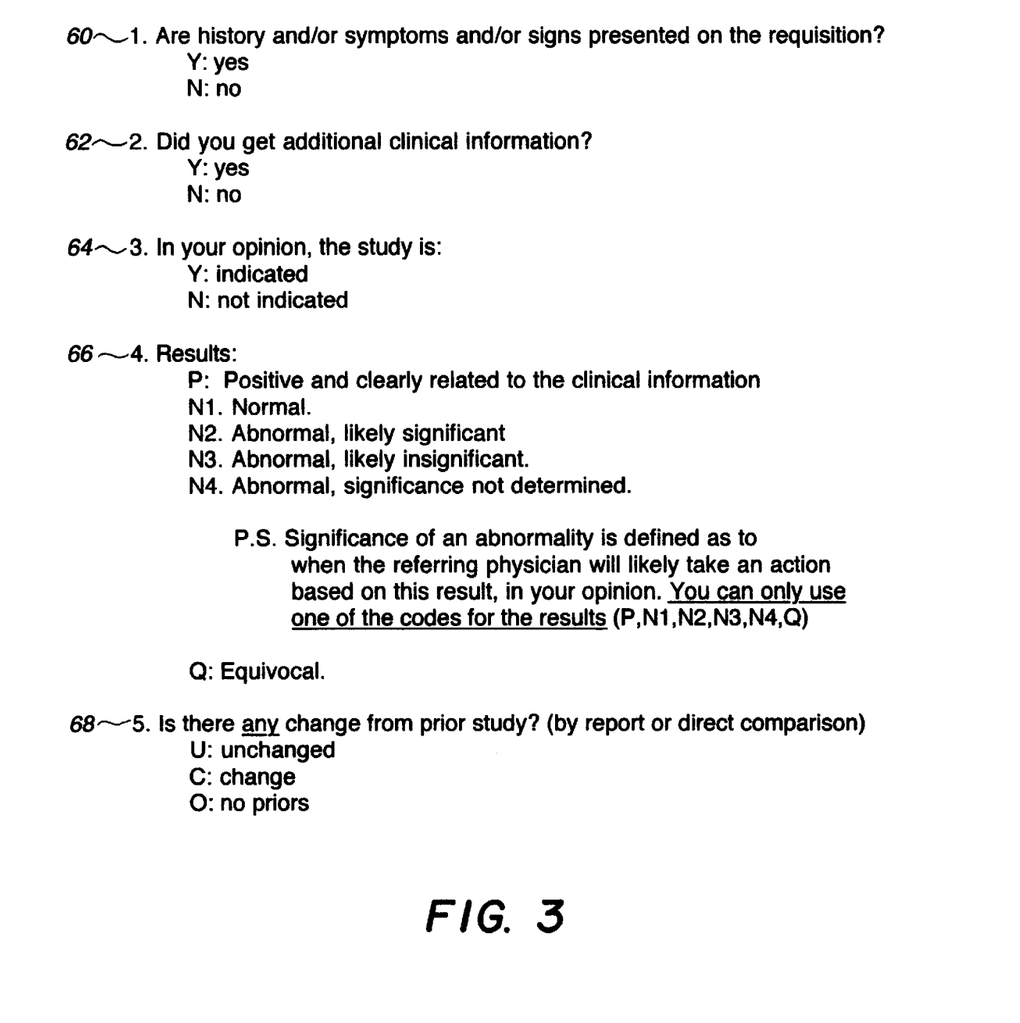
FIG. 3 illustrates a graphical user interface for entry of result codes from studies performed on a patient.

A graphical user interface using the Netscape browser for inputting result codes for a given study for a patient is shown in FIG. 3. As an example, the user interface may present five questions 60–68. Each of the responses, of which only one may be selected for each question, is recorded in the structure 30. One of these queries, e.g., the fourth question 66, is used as the basis for measuring the appropriateness of a study given study. A letter "P", signifying positive and clearly related results to the clinical information, is the value that is counted to determine the relative relevance of a study to a given indication.

Figure 4:
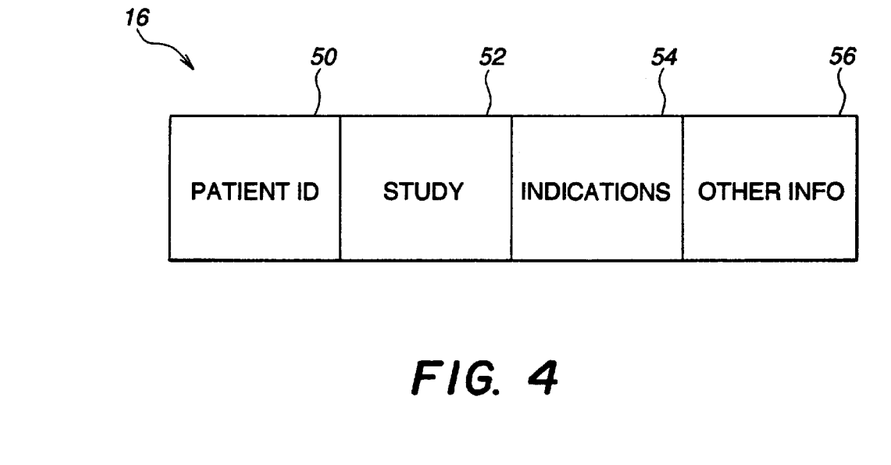
FIG. 4 is an illustration of a data record representing a request for a study to be performed on a patient.

FIG. 4 illustrates a sample order as illustrated at 16 in FIG. 1. The order 16 includes an identifier 50 of a patient, the specified study 52, the indications 54 for the study and possibly other information 56. This record may be stored in a variety of forms for transmission from the structured ordered entry module 12 to the decision support module 18. For example, the order information may be stored as an HTML form that is input using an HTML document in a browser such as the Netscape Navigator HTML browser from Netscape Communications, Inc. The HTML document and the HTML browser may be used to implement the structured order entry module 12.

Figure 5:
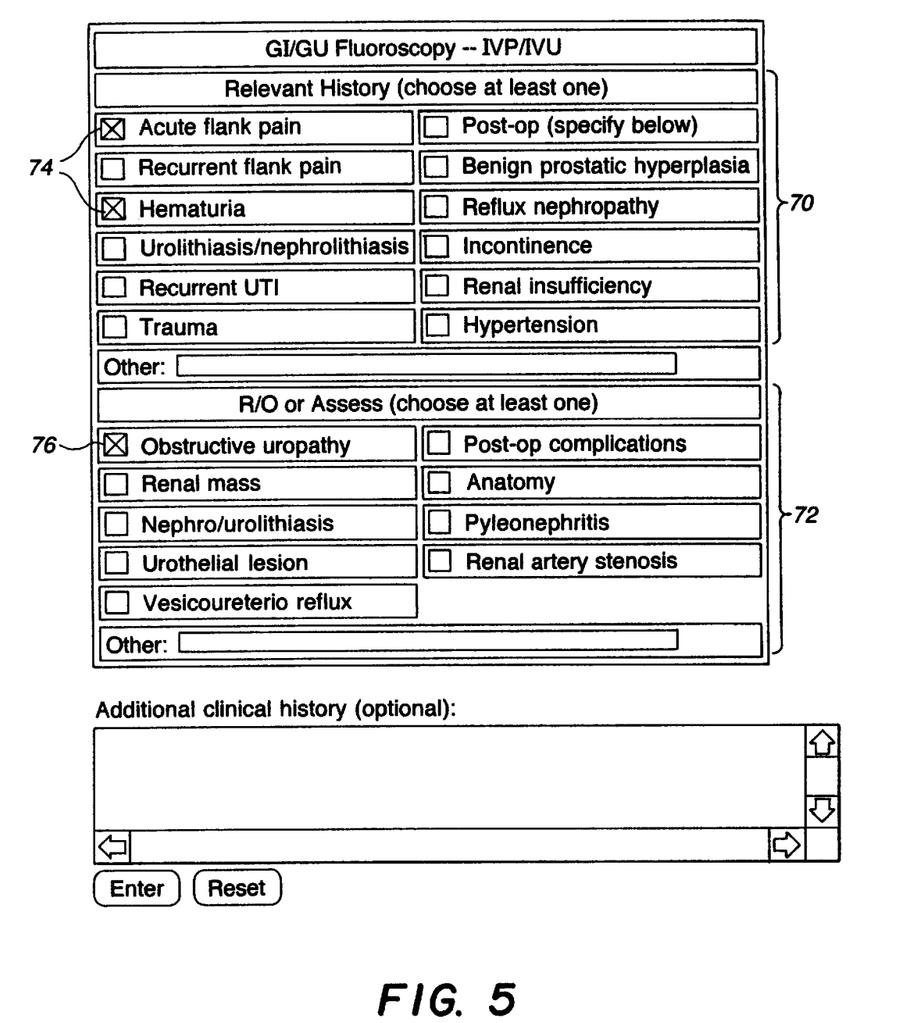
FIG. 5 illustrates a graphical user interface for providing structured order entry of studies for patients.

An example graphical user interface using an HTML browser for the structured order entry is shown in FIG. 5. The user interface may provide a menu-type selection to allow an ordering physician to select one of several kinds of studies. Given the selection of a particular kind of study, additional menus are shown. First, an ordering physician is allowed to indicate relevant history as shown at 70. In addition, other indications for study may be specified as shown at 72. Using this information, it is possible to select, for example, acute flank pain and hematuria as relevant history as shown at 74, and to select the indication for the study as diagnosis of obstructive uropathy, as shown at 76. The selected study, patient history, and the specified indications for the selected study are processed through this interface to generate an order for submission to the decision support system.

Figure 6:
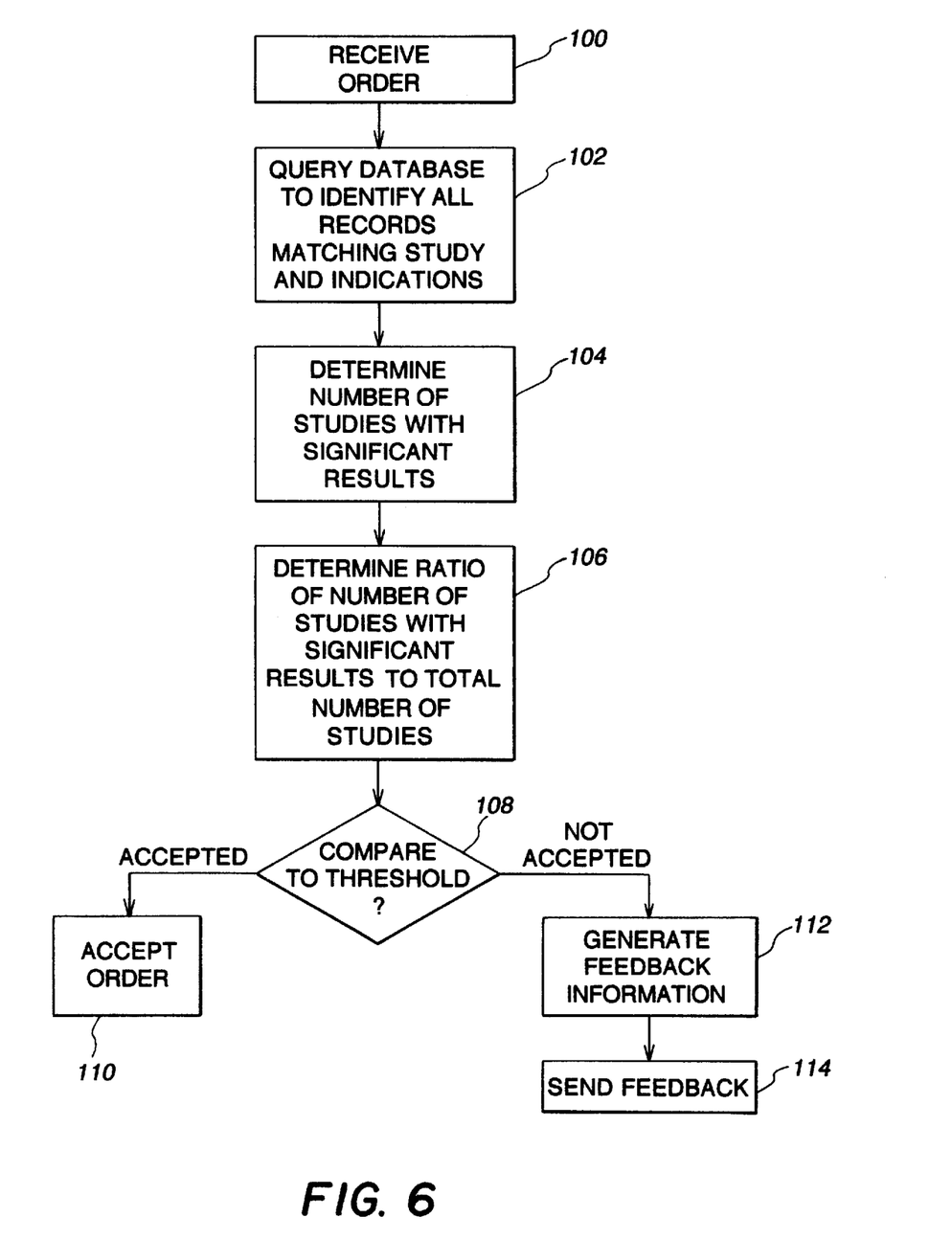
FIG. 6 is a flowchart describing the decision support process.

FIG. 6 is a flowchart describing processing performed by decision support module 18 in one embodiment of the present invention. The decision support module receives an order in step 100. The database is then queried in step 102 for all records matching the selected study and the specified indications for the study in the received order. The total number of records is counted. The number of records within the retrieved set, for which the result code signifies that the study findings were significant and related to the clinical information, is then determined in step 104. A ratio, or other measure of the relation of this number to the total number of studies is determined in step 106. This value may be compared to a threshold, as shown in step 108, to determine whether the request should be accepted. If accepted, feedback is provided to the ordering physician in step 110. If the order is not accepted, or if steps 108 and 110 are omitted, appropriate feedback information is generated in step 112. This feedback information may be in several forms. For example, it may indicate the percentage of studies with significant results out of the total number of studies. This percentage may be fed back to the ordering physician as shown at feedback 24 in FIG. 1. An alternative study might be suggested, for example, by reference to data extracted from existing scientific literature stored in the database, or by searching the database for other studies having the same indications but more significant results. Decision support may be enhanced, where available, by this data extracted from existing scientific literature about the selected study and the same specified indications for the study. The ordering physician may be asked whether or not to continue with the requested study or to cancel the request. Alternatively, the request simply may be refused and this refusal may be communicated to the ordering physician. The feedback is sent to the ordering physician in step 114.

Figure 7:
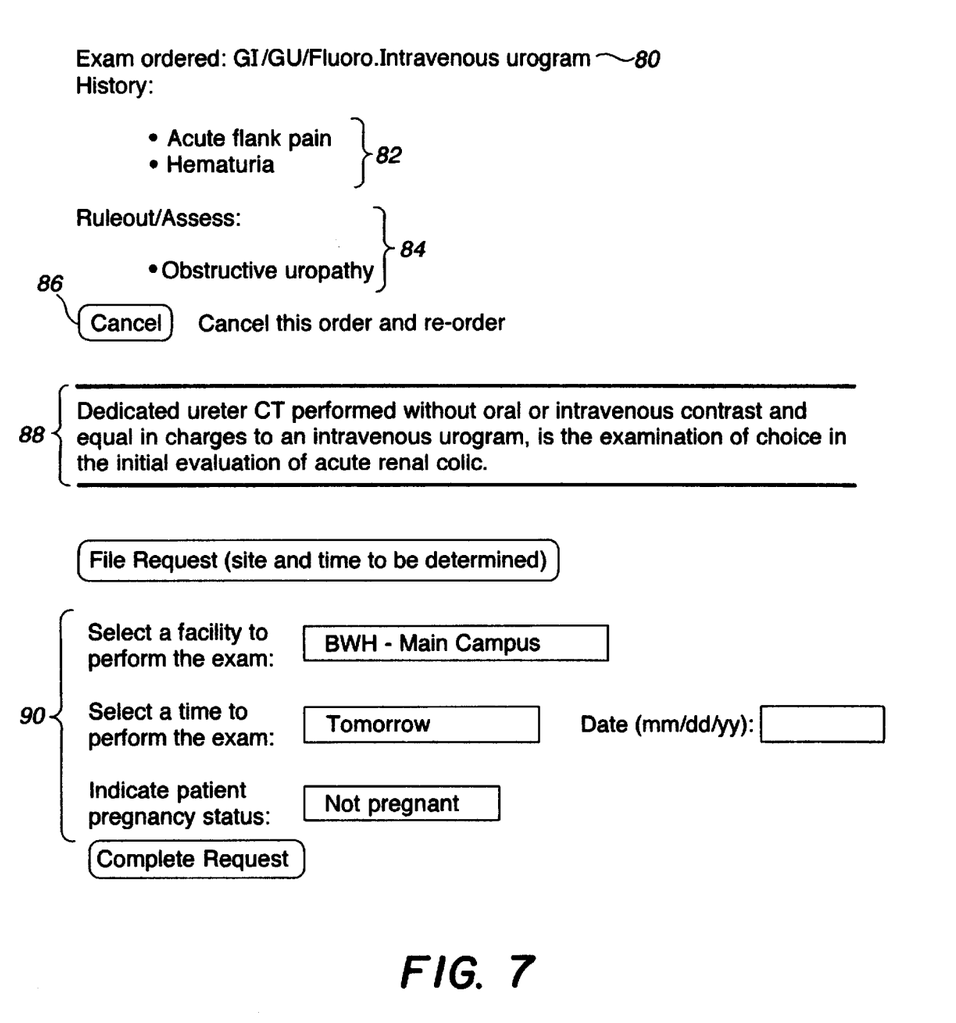
FIG. 7 is a graphical user interface of feedback provided to an ordering physician.

FIG. 7 is a diagram of a graphical user interface in one embodiment of the invention that provides the feedback to the ordering physician. The user interface indicates the study ordered at 80, the specified history at 82 and the specified indications for the study at 84. An opportunity to cancel the order is presented at 86, for example, in the form of a button. The feedback to the ordering physician is provided at 88. In this example, it is shown that if obstructive uropathy is suspected in a patient with acute flank pain and hematuria, then an intravenous urogram should be superseded by ureter computer tomography (CT) which is the examination of choice in the initial evaluation of acute renal colic. Alternatively, it is possible to complete the request by providing more information as indicated at 90, including the ability to select facility to perform the study, a time, and other patient information.

By continued use of the present system, the result codes database will grow in the amount of information available and the appropriateness of various studies with respect to actual patient outcomes will become more apparent. Feedback provided will advise ordering physicians that certain studies are not likely to provide them valuable information and ordering physician behavior will gradually change. In addition, use of this system enables enforcement as well as behavior modification to occur. As a result, this managed utilization of various diagnostic studies can reduce costs.

Having now described a few embodiments of the invention, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention as defined by the appended claims and equivalent thereto.

We claim:

1. A decision support system in a health care information management system, comprising:

means for receiving from an ordering physician an order for a selected study to be performed on a specified patient, wherein the order includes specified indications for the study;

means for identifying result codes, in a database associating previous studies performed on patients including patients other than the specified patient and indications for the previous studies with result codes corresponding to results of the previous studies, according to the selected study and the specified indications, the identified result codes corresponding to results of previous studies having the specified indications and performed on patients including patients other than the specified patient; and means for communicating to the ordering physician the identified result codes.

2. The decision support system of claim 1, wherein the means for identifying comprises:

means for identifying a total number of records in the database corresponding to the selected study and specified indications;

means for identifying a number of records with significant results out of the identified records; and means for determining a ratio of the number of records with significant results to the total number of records corresponding to the selected study and specified indications.

3. A health care information management system, comprising:

a structured order entry module having inputs for receiving data from an input device activated by an individual and an output for providing an order including a selected study and specified indications for the study for a patient;

a database associating previous studies performed on patients including patients other than the specified patient and indications for the previous studies with result codes corresponding to results of the previous studies; and a decision support module, including:

means for receiving the order from the structured order entry module;

means for identifying result codes in the database according to the selected study and the specified indications, the selected result codes corresponding to results of previous studies having the specified indications and performed on patients other than the specified patient; and means for communicating to the ordering physician the identified result codes.

4. The health care information management system of claim 3, further comprising:

a test result codes input module having an input for receiving data from an input device activated by an individual and an output for providing and storing result codes in the database.

5. The health care information management system of claim 4, wherein the means for identifying of the decision support module comprises:

means for identifying a total number of records in the database corresponding to the selected study and specified indications;

means for identifying a number of records with significant results out of the identified records; and means for determining a ratio of the number of records with significant results to the total number of records corresponding to the selected study and specified indications.

6. The health care information management system of claim 3, wherein the means for identifying of the decision support module comprises:

means for identifying a total number of records in the database corresponding to the selected study and specified indications;

means for identifying a number of records with significant results out of the identified records; and means for determining a ratio of the number of records with significant results to the total number of records corresponding to the selected study and specified indications.

7. A method for providing decision support in a health care information management system, the method comprising steps of:

receiving from an ordering physician an order for a selected study to be performed on a specified patient, wherein the order includes specified indications for the study;

identifying result codes, in a database associating previous studies performed on patients including patients other than the specified patient and indications for the previous studies with result codes corresponding to results of the previous studies, according to the selected study and the specified indications, the identified result codes corresponding to results of previous studies having the specified indications and performed on patients including patients other than the specified patient; and communicating to the ordering physician the identified result codes.

8. The method of claim 7, wherein the step of identifying comprises steps of:

identifying a total number of records in the database for the selected study and specified indications;

identifying a number of records with significant results out of the identified records; and determining a ratio of the number of records with significant results to the total number of records for the selected study and specified indications.

9. A decision support system in a health care information management system, comprising:

means for receiving from an ordering physician an order for a selected study to be performed on a specified patient, including specified indications for the study;

means for comparing the specified indications for the selected study to a database of result codes for previous studies having the same indications and performed on patients including patients other than the specified patient, the means for comparing comprising:

means for identifying a total number of records in the database for the selected study and specified indications;

means for identifying a number of records with significant results out of the identified records; and means for determining a ratio of the number of records with significant results to the total number of records for the selected study and specified indications; and means for communicating to the ordering physician a result of the comparison of the specified indications for the selected study with the result codes.

10. A health care information management system, comprising:

a structured order entry module having inputs for receiving data from an input device activated by an individual and an output for providing an order including a selected study and specified indications for the study for a patient;

a database of result codes for previous studies performed on patients including patients other than the specified patient;

a decision support module, including:

means for receiving the order from the structured order entry module;

means for comparing the specified indications of the selected study to the database, comprising means for identifying a total number of records in the database for the selected study and specified indications, means for identifying a number of records with significant results out of the identified records; and means for determining a ratio of the number of records with significant results to the total number of records for the selected study and specified indications; and means for communicating to the ordering physician a result of the comparison of the specified indications for the study with the database; and a test result codes input module having an input for receiving data from an input device activated by an individual and an output for providing and storing result codes in the database.

11. A health care information management system, comprising:
- a structured order entry module having inputs for receiving data from an input device activated by an individual and an output for providing an order including a selected study and specified indications for the study for a patient;
- a database of result codes for previous studies performed on patients including patients other than the specified patient; and
- a decision support module, including:
  - means for receiving the order from the structured order entry module;
  - means for comparing the specified indications of the selected study to the database, comprising means for identifying a total number of records in the database for the selected study and specified indications, means for identifying a number of records with significant results out of the identified records, and means for determining a ratio of the number of records with significant results to the total number of records for the selected study and specified indications; and
  - means for communicating to the ordering physician a result of the comparison of the specified indications for the study with the database.

* * * * *